United States Patent [19]

Stemberger

[11] 4,407,787

[45] Oct. 4, 1983

[54] COLLAGENOUS DRESSING

[75] Inventor: Axel Stemberger, Neubiberg, Fed. Rep. of Germany

[73] Assignee: Dr. Ruhland Nachf. GmbH, Neustadt, Fed. Rep. of Germany

[21] Appl. No.: 303,851

[22] Filed: Sep. 21, 1981

[30] Foreign Application Priority Data

Oct. 3, 1980 [DE] Fed. Rep. of Germany ....... 3037513

[51] Int. Cl.³ .................. A61F 13/00; C08L 89/00; A61K 35/14; A61K 37/00
[52] U.S. Cl. ..................................... 424/28; 106/122; 106/125; 106/128; 106/161; 128/156; 424/101; 424/177; 424/180
[58] Field of Search .............. 424/28, 15, 27, 177, 424/180, 215, 175; 106/125, 128, 161, 122; 128/156

[56] References Cited

U.S. PATENT DOCUMENTS 3,106,483 10/1963 Kline et al. ......................... 424/27
3,666,750 5/1972 Briskin et al. ....................... 424/180
4,148,664 4/1979 Cruz .................................... 106/161

OTHER PUBLICATIONS

Chemical Abstracts 77:76514f, "Collagen Fibers", Vasil'ev, 1972.
Chemical Abst. 66:44064r, Klemm, "Enhanced Healing of Skin Wounds in Dogs with Systematically and Locally Administered Drugs".

*Primary Examiner*—Theodore Morris
*Attorney, Agent, or Firm*—Curtis, Morris & Safford

[57] ABSTRACT

A collagenous dressing which is characterized in that it contains collagen in combination with a resorbable biopolymer from the group comprising fibrinogen, gelatin modified by SH groups, collagen modified by SH groups, or regenerated oxycellulose modified by SH groups. Said collagenous dressing is tissue-agglutinable and does not have the disadvantages of conventional fibrin bonding in combination with resorbable collagen.

12 Claims, No Drawings

COLLAGENOUS DRESSING

Collagen has been used in surgery for some time. It can be used in the form of sponges or fibers to control bleeding and, properly modified, is suited also to promote the healing of wounds. However, in the case of patients with defective clotting mechanism, or in the case of bleeding over a large area, the usual collagenous dressings are inadequate. Attempts have therefore been made to bond collagenous material, such as collagen or gelatin, to tissue by the use of adhesives based on resorcinol-formaldehyde. While such adhesives are hemostatic, they are not suited for practical use because of their tissue irritation. This is true also of acrylate adhesives and their combination with collagenous dressings.

It is known that collagen in the body is crosslinked with constituents of connective tissue. In the process, collagen is crosslinked through Schiff bases and aldol condensation. It is further known that in basal membranes tissue strength is enhanced through disulfide bridges of the basal membrane collagen. It is also known to crosslink proteins such as albumin with intermolecular disulfide bonds through disulfide bridges after mild reduction followed by oxidation. In injuries, blood clotting forms a primary closure of the wound. This is due to aggregated thrombocytes and a fibrin network during the end phase of the plasmatic coagulation. It is also known that individual fibrin molecules are crosslinked through transglutaminase. In the process, new peptide bonds are formed between glutamic acid and lysine respectively located on adjacent chins. Through the technique of fibrin bonding, in other words, the use of fibrinogen and thrombin, the end phase of plasmatic blood clotting is imitated. Fibrin bonding alone cannot control bleeding over a large area. This becomes possible only through a combination of fibrin bonding and a resortable collagenous dressing. However, three components must be kept in readiness: The collagenous dressing, thrombin solution with antifibrinolytic agents, and a deep-frozen highly concentrated fibrinogen solution ready for use only after thawing. Since bleeding frequently occurs suddenly and unexpectedly, the fibrinogen component of the three components is often not available at the critical moment in a form ready for use since at least the deep-frozen fibrinogen solution must first be thawed. Moreover, mixing prior to application is relatively complicated.

The object of the invention is to provide a collagenous dressing which will conglutinate with (ie. adhere to) the tissue and which does not have the known drawbacks of fibrin bonding in combination with resorbable collagen. Coupled with this object is an improvement to collagenous dressings for local hemostasis.

This object is accomplished through a tissue-adherent collagenous dressing which is characterized in that it contains collagen in combination with a resorbable biopolymer from the group comprising fibrinogen, gelatin modified to contain SH groups, collagen modified to contain SH groups, or oxycellulose modified to contain SH groups.

Collagen and fibrinogen or the gelatin modified by SH groups, similarly modified collagen or similarly modified oxycellulose may advantageously be combined with each other through freeze drying. However, in the case of a combination of collagen and collagen modified to contain SH groups it is also possible to introduce SH groups into the collagen.

The invention will now be described with reference to a combination of collagen and fibrinogen; however, fibrinogen here takes the place of said resorbable biopolymers, namely, gelatin modified to contain SH groups, collagen modified to contain SH groups, or oxycellulose modified to contain SH groups.

The occasional occurrence of hepatitis poses a problem in the application of fibrinogen. Of course, this problem can be avoided altogether by introducing, not fibrinogen but other biopolymers containing reactive SH groups. Such biopolymers containing SH groups are gelatin modified to contain SH groups, regenerated oxycellulose modified to contain SH groups, or collagen modified to contain SH groups.

The introduction of SH groups into collagen may be effected in a manner which per se is known. For example, the procedure set forth by Benesch & Benesch in "Proceedings of the National Academy of the United States, Washington, D.C.", vol. 44 (1958), pp. 848–853, may be followed.

However, SH groups can also be introduced into collagen by depositing a gelatin modified by SH groups, or a similarly modified regenerated oxycellulose, on collagen or mixing it therewith by means of a gradient mixer. Gelatin is formed from collagen through chemical or enzymatic decomposition and thus has the same chemical composition. Consequently, collagenous dressings provided with gelatin modified to contain SH groups essentially also have the properties of collagen along with the advantage that because of the SH groups in these materials oxidative crosslinking is able to occur.

The collagenous dressings in accordance with the invention may incorporate active substances, in a manner which is known per se.

The collagen used as a dressing has the usual form of dressings, i.e., gauze, cloth, sponge, etc.

The purity of the collagen used, expressed as a ratio of nitrogen-to-hydroxyproline, is less than 4, and preferably less than 3. Since hydroxyproline occurs only in collagen, this is a measure for the purity of the collagen.

The resorbable biopolymer is present in the tissue-adherent collagenous dressing in an amount ranging from 0.5 to 10 $mg/cm^2$, and preferably from 4 to 6 $mg/cm^2$. The number of SH groups per molecule of resorbable biopolymer may vary over a wide range. For gelatin of an average molecular weight of about 40,000 it is about 2 to 7 and on the average about 5, and for the other resorbable biopolymers it is of the same order of magnitude.

It is known that collagen is suitable for use as a vehicle for antibiotics such as gentamycin. Tetracycline or other antibiotics or chemotherapeutic agents may also be worked into the collagen modified to contain SH groups. This is an additional effect that can be obtained with the dressings in accordance with the invention.

PREPARATION OF COLLAGENS

Fresh bovine tendons which had been freed of all pigment layers and muscular residues were homogenized, and an amount corresponding to 100 g dry weight was extracted for 24 hours in 3 liters of 0.05 M citrate buffer (pH 3.7) and then dialyzed for 12 hours against 1% acetic acid.

The tissue, suspended in 3 liters 1% acetic acid, was incubated for 48 hours at 15° C. with constant stirring, with pepsin in a collagen-to-pepsin ratio of 50:1.

The batch was diluted with 1% acetic acid to 5 liters and freed of undissolved tendom fragments by centrifugation.

The viscous collagen solution was dialyzed against alkalinized tap water (pH 8.0) and then vigorously centrifuged. The residue was again dissolved in 5 liters 1% acetic acid and dialyzed. This procedure was repeated until the nitrogen-to-hydroxyproline ratio was less than 3. After the last dialysis, a 1.5% collagen solution was prepared by means of 0.05% acetic acid, which was then used in the tests described below.

PREPARATION OF AN SH-MODIFIED GELATIN, AN SH COLLAGEN, OR AN SH REGENERATED OXYCELLULOSE 1000 ml of a 2% gelatin solution (a corresponding recipe applies to a 1.5% collagen solution or to a suspension of 50 g collagen or regenerated oxycellulose) was mixed at pH 7.0 with 318 mg N-acetylhomocysteinethiolactone, following which 340 mg AgNO$_3$ was added, the solution being maintained at pH 7.0 by the addition of NaOH.

After 2 hours, the pH was adjusted to 2.5 with 1 N HCl, and thiourea was added in excess. The silver ions were removed by means of a cation exchanger and the solution was dialyzed under nitrogen. 1% solutions of the SH-modified gelatin and of the SH-modified collagen were then prepared for the tests described below.

The regenerated oxycellulose was dehydrated by lyophilization.

PREPARATION OF FIBRINOGEN SOLUTIONS

Commercially available sterile fibrinogen in bulk was dissolved in sterile distilled water to give a solution of 50 mg fibrinogen/ml of solution, which was used in the tests described below.

EXAMPLE 1

Preparation of a collagen/fibrinogen-containing dressing of about 2.5×5.0 cm

Of a 1.5% collagen solution sterilized by irradiation, 10 ml was introduced under aseptic conditions into a sterile bottle having a septum and deep-frozen in a cold bath (dry ice/ethanol) with mild agitation. After about two-thirds of the solution had frozen, 5 ml of a collagen/fibrinogen solution (collagen-to-fibrinogen ratio, 1:1) was added and also deep-frozen until two-thirds of the solution was frozen. Following this, 5 ml of the fibrinogen solution was added, deep-frozen, and lyophilized.

EXAMPLE 2

Preparation of a dressing containing collagen and SH-modified gelatin

Of a 1.5% collagen solution, 10 ml was introduced into a bottle having a septum and deep-frozen in a cold bath (dry ice/ethanol) with mild agitation. After about two-thirds of the solution had frozen, 10 ml of the SH-modified gelatin solution was added, deep-frozen, and lyophilized. This sponge was then sterilized by irradiation.

EXAMPLE 3

Preparation of gentamycin-containing dressings

For the preparation of gentamycin-containing dressings, 100 mg gentamycin was added to 100 ml of a 1% collagen solution, and this solution was used as described above to prepare a collagen/fibrinogen-containing dressing and a collagen/SH-gelatin-containing dressing.

EXAMPLE 4

Preparation of dressings containing collagen and fibrinogen

First 100 ml of an 0.5 to 1% collagen solution was poured into a metallic mold and conventionally freeze-dried, and the sponge so produced was sterilized. This sterilized collagen sponge was then spray-coated under aseptic conditions with a fibrinogen solution, from 0.5 to 10 mg fibrinogen per square centimeter of collagen surface being so deposited. Freeze-drying was then repeated and packaging effected under sterile conditions.

In the practical use of the modified tissue-agglutinable collagenous dressings in accordance with the invention, resorption occurs within clinically appropriate periods of time. In accordance with the invention, they can be used to dress even large-area wounds, especially in the abdominal region.

I claim:

1. A tissue-adherent collagenous dressing, comprising collagen present in combination with a resorbable biopolymer from the group consisting of fibrinogen, gelatin modified to contain reactive SH groups, collagen modified to contain reactive SH groups, and regenerated oxycellulose modified to contain reactive SH groups.

2. A tissue-adherent collagenous dressing according to claim 1, further comprising a medicinally active agent.

3. A tissue-adherent collagenous dressing according to claim 2, wherein the medicinally active agent is an antibiotic.

4. A tissue-adherent collagenous dressing, according to claim 3, wherein the antibiotic is gentamycin.

5. A tissue-adherent collagenous dressing, according to one of the preceding claims, wherein the collagen is present in the form of a cloth.

6. A tissue-adherent collagenous dressing, according to one of claims 1 to 4, wherein the collagen is present in the form of a sponge.

7. A tissue-adherent collagenous dressing according to claim 1, wherein the purity of the collagen, expressed by the nitrogen-to-hydroxyproline ratio, is less than 4.

8. A tissue-adherent collagenous dressing according to claim 1, wherein the purity of the collagen, expressed by the nitrogen-to-hydroxyproline ratio, is less than 3.

9. A tissue-adherent collagenous dressing according to claim 1, wherein said biopolymer is fibrinogen.

10. A tissue-adherent collagenous dressing according to claim 1, wherein said biopolymer is gelatin modified to contain reactive SH groups.

11. A tissue-adherent collagenous dressing, comprising collagen present in combination with resorbable collagen modified to contain reactive SH groups.

12. A tissue-adherent collagenous dressing, comprising collagen present in combination with resorbable regenerated oxycellulose modified to contain reactive SH groups.

* * * * *